(12) United States Patent
Farng et al.

(10) Patent No.: US 8,426,474 B2
(45) Date of Patent: Apr. 23, 2013

(54) ANTIMICROBIAL WASH AND CARRIER SOLUTIONS AND USES THEREOF

(75) Inventors: Richard Farng, Miramar, FL (US); Steven Mrha, Cooper City, FL (US)

(73) Assignee: Teva Animal Health, Inc., St. Joseph, MO (US)

( * ) Notice: Subject to any disclaimer, the term of this patent is extended or adjusted under 35 U.S.C. 154(b) by 226 days.

(21) Appl. No.: 13/048,262

(22) Filed: Mar. 15, 2011

(65) Prior Publication Data

US 2011/0166105 A1 Jul. 7, 2011

Related U.S. Application Data

(62) Division of application No. 10/412,477, filed on Apr. 11, 2003, now Pat. No. 7,928, 147.

(60) Provisional application No. 60/371,755, filed on Apr. 11, 2002.

(51) Int. Cl.
| | |
|---|---|
| *A61K 31/045* | (2006.01) |
| *A61K 31/13* | (2006.01) |
| *A61K 31/195* | (2006.01) |
| *A61K 31/74* | (2006.01) |
| *A61K 31/765* | (2006.01) |
| *A61K 47/00* | (2006.01) |
| *A61K 47/30* | (2006.01) |

(52) U.S. Cl.
USPC ............... 514/730; 424/78.05; 424/78.37; 424/DIG. 6; 514/566; 514/669; 514/673; 514/727; 514/772.3; 514/784; 514/788; 514/887

(58) Field of Classification Search .............. 514/730
See application file for complete search history.

(56) References Cited

U.S. PATENT DOCUMENTS

| | | |
|---|---|---|
| 3,758,682 A | 9/1973 | Huber et al. |
| 5,480,658 A | 1/1996 | Melman |
| 5,597,560 A | 1/1997 | Bergamini et al. |
| 5,631,218 A | 5/1997 | Allan et al. |
| 5,641,480 A | 6/1997 | Vermeer |
| 5,853,767 A | 12/1998 | Melman |
| 5,928,631 A | 7/1999 | Lucas et al. |
| 6,211,238 B1 | 4/2001 | Castillo et al. |
| 6,214,363 B1 | 4/2001 | Beerse et al. |
| 6,284,749 B1 | 9/2001 | Castillo et al. |
| 6,440,437 B1 | 8/2002 | Krzysik et al. |
| 2002/0091074 A1 | 7/2002 | Wooley et al. |
| 2003/0022941 A1 | 1/2003 | Taylor et al. |
| 2003/0069317 A1 | 4/2003 | Seitz, Jr. et al. |

FOREIGN PATENT DOCUMENTS

WO  WO-02/24143 A2  3/2002

OTHER PUBLICATIONS

I. Reich et al., Chapter 36: Tonicity, Osmoticity, Osmolality and Osmolarity, *Remington: The Science and Practice of Pharmacy*, $19^{th}$ ed. (Easton, Pennsylvania: Mack Publishing Company, 1995), pp. 613-627.
*The Pharmacological Basis of Therapeutics*, ed. Goodman et al., $5^{th}$ ed. (New York: Macmillan Publishing, 1975), p. 994.
*Handbook of Pharmaceutical Excipients*, $2^{nd}$ ed., ed. Wade et al., (London: The Pharmaceutical Press, 1994), pp. 35-37.
L. Z. Benet et al., Chapter 1: Pharmacokinetics: The Dynamics of Drug Absorption, Distribution, and Elimination, *Goodman and Gilman's The Pharmacological Basis of Therapeutics*, $8^{th}$ ed. (Pergamon Press, 1980), pp. 3-32.
L. K. Cole et al., "In vitro activity of an ear rinse containing tromethamine, EDTA, and benzyl alcohol on bacterial pathogens from dogs with otitis," *AJVR*, vol. 67, No. 6, Jun. 2006, pp. 1040-1044.
DermaPet® Newsletter, Mar. 2006, http://www.dermapet.com/news/news-76.html.
A. M. Farca, G. Piromalli, R. Maffei, and G. Re, "Potentiating effect of EDTA-Tris on the activity of antibiotics against resistant bacteria associated with otitis, dermatitis and cystitis,"*Journal of Small Animal Practice*, 1997, 38: 243-245.

*Primary Examiner* — John Pak
*Assistant Examiner* — Nathan W Schlientz
(74) *Attorney, Agent, or Firm* — RatnerPrestia

(57) ABSTRACT

Novel wash and carrier solutions ideally suited for topical administration (e.g., as wash solutions and as carrier solutions). The solutions described herein are non-toxic, non-irritating, isotonic, possess non-specific broad-spectrum antimicrobial properties, and have an alkaline pH. Also disclosed are sterile preparations of the solutions and methods of using the same.

8 Claims, No Drawings

ANTIMICROBIAL WASH AND CARRIER SOLUTIONS AND USES THEREOF

CROSS-REFERENCE TO RELATED APPLICATIONS

This application is a divisional of U.S. patent application Ser. No. 10/412,477, filed Apr. 11, 2003, and claims priority of U.S. Provisional Application No. 60/371,755, filed Apr. 11, 2002, the disclosures of all of which are incorporated herein by reference in their entirety for all purposes.

BACKGROUND OF THE INVENTION

1. Field of the Invention

The invention relates to the field of topical antimicrobial wash and carrier solutions. The solutions disclosed herein are substantially non-irritating and thus, are especially suited to deliver topically pharmaceutical active agents, to clean and/or treat wounds or tissues.

2. Description of the Related Art

A variety of antimicrobial wash and carrier solutions are currently used to wash skin or other tissue surfaces, including wounds, to remove dirt, debris, or to loosen or soften crusted lymph or blood clots. In some instances, such solutions are used to disinfect a tissue and thus, curb or prevent an infection. In addition, such solutions can be used as carriers for pharmaceutically active agents to be topically applied to a given tissue.

Under normal circumstances (i.e., in the absence of heightened pain sensitivity) a wash solution should preferably be non-irritating. The tissues treated with wash solutions are often inflamed and thus, have a heightened sensitivity to pain, compelling the use of non-irritating substances. Unfortunately, a great number of wash solutions presently available elicit tissue irritation, making their use in the pediatric and veterinary setting cumbersome. For the most part, non-specific disinfectant/antimicrobial solutions (e.g., solutions including acetic acid) described in the art may actually cause or exacerbate tissue irritation at the site of use because of their nature and/or effective concentration or treatment time required.

Solutions, which differ from normal serum in tonicity, have been shown to cause pain on injection, electrolyte shifts, or even tissue irritation following contact. This effect depends on the degree of deviation from isotonicity. For example, ophthalmic preparations for instillation in the eye should be isotonic in nature to avoid irritation. Therefore, wash solutions should be isotonic in nature to avoid exacerbation of irritation associated with tissue damage (see e.g., *Remington: The Science and Practice of Pharmacy*, 19$^{th}$ Ed., Ch., 36, Gennaro, A. R., Ed, Mack Publishing Co. (1995)).

Wash solutions have been used as carrier solutions by supplementing them, for example, with one or more antibiotic(s). Moreover, combinations of Tris-EDTA solutions with specific antibiotics have been postulated to have a synergistic effect against a variety of infectious agents and have been described extensively in the literature at least as early as 1974 (see for example Blue et al. (1974), Wooley et al. (1983), Farca et al. (1997), see also PCT/US01/29133 describing various formulations for the treatment of specific Gram positive and Gram negative bacterial infections using Tris-EDTA, a variety of antibiotics, and a carrier). However, quite often the effectiveness of this well-known approach is hampered by the development of microbial antibiotic resistance.

An ideal wash/carrier solution should also be a non-specific broad-spectrum antimicrobial for initial use until the specific infection is identified, and subsequently as a carrier (e.g., for antibiotics). Non-specific broad-spectrum antimicrobial properties are useful (a) to aid in cleansing and treating the underlying tissue (e.g., to treat an existing infection or prevent an infection); and (b) to minimize and preferably even prevent the occurrence of back contamination of a multi-dose dispenser, thereby minimizing inadvertent cross-contamination from use to use and/or from user to user.

Several solutions described in the literature include a rather harsh disinfecting agent such as boric acid which are known to be toxic (boric acid has been removed from many hospitals after reports showed that repeated applications to damaged tissues resulted in the absorption of boric acid in sufficient amounts to cause acute poisoning causing death in half of the patients accidentally intoxicated (Goodman and Gilman's *The Pharmacological Basis of Therapeutics*, 5$^{th}$ Ed., Ch. 50, page 994, McGraw Hill Companies Inc., New York (1975)). To exemplify, U.S. Pat. No. 5,480,658 describes a "pH balanced"—e.g., alkaline pH—multi-purpose cleaning solution containing acetic acid and boric acid in a water base for the routine cleaning of the ear, the prevention and treatment of ear disease such as "swimmer's ear," and wound cleaning. Similarly, U.S. Pat. No. 5,853,767 discloses a solution comprising, as active ingredients, both acetic acid and boric acid for the treatment of bacterial and fungal skin infections. The solution is described as having bacteriostatic, bacteriocidal and anti-fungal properties, and as useful for the treatment of vaginal infections, such as vaginitis.

The alkaline pH is useful for conditioning and softening biological tissues, and increasing the penetration of pharmaceutical agents. The exudates associated with infected lesions are acidic in nature and can inactivate or reduce the efficacy of many commonly used antibiotic agents. An alkaline pH wash solution can aid in the neutralization of the acidic environment of the lesion thereby allowing for increased efficacy for the commonly used antibiotic agents. Unfortunately, several solutions described to date are acidic. U.S. Pat. No. 5,631,218 is to a disinfecting solution including an ortho-hydroxy benzoic acid derivative (e.g., salicylic acid) and an amphoteric surfactant and/or an alkoxylated alcohol nonionic surfactant (e.g., an ethoxylated alcohol). The solution has a pH of 1.0-5.5. Similarly, U.S. Pat. No. 6,214,363 discloses a rinse-off antimicrobial cleansing composition including an antimicrobial agent, an anionic surfactant, a proton donating agent, and a deposition aid in water, in which the composition is adjusted to a pH of from about 3.0 to about 6.0.

Other solutions described in the art include U.S. Pat. No. 6,211,238 disclosing anionic surfactants that are used in conjunction with an antifungal acid and a chelating agent to preserve topically administrable pharmaceutical compositions without the need for a conventional preservative, such as benzalkonium chloride. U.S. Pat. No. 6,284,749 discloses a preservative system for topically administrable pharmaceutical compositions including fatty acid/amino acid soaps in conjunction with an antifungal acid and a chelating agent.

Thus, there is a need for wash and carrier solutions overcoming the shortcomings of presently available solutions. Such wash and carrier solutions ideally should be non-toxic, non-irritating, isotonic, possess non-specific broad-spectrum antimicrobial properties, and have an alkaline pH.

SUMMARY OF THE INVENTION

The inventors have devised novel wash and carrier solutions ideally suited for topical administration (e.g., as wash solutions and as carrier solutions). The solutions described herein are non-toxic, non-irritating, isotonic, possess non-specific broad-spectrum antimicrobial properties, and have an alkaline pH.

Thus, in one aspect, the present invention provides a non-irritating aqueous antimicrobial and preservative wash and carrier solution, for use as a wash solution for biological tissues or a carrier solution for delivering pharmaceuticals to biological tissues, including (a) a buffer system for maintaining the solution at an alkaline pH, (b) a surfactant system, (c) a metal ion chelating agent, and (d) a non-ionic preservative having antimicrobial activity.

In some embodiments, the buffer system is a Tris buffer system, a phosphate buffer system, or a citrate buffer system. In certain embodiments, the buffer system is a Tris buffer system including tromethamine base at a concentration of about 0.1-2.0 (w/w) and tromethamine hydrochloride at a concentration of about 0.1-2.0 (w/w). In an embodiment the Tris buffer system according to the invention includes tromethamine base at a concentration of about 0.45-0.55 (w/w). In yet another embodiment, the Tris buffer system according to the invention includes tromethamine hydrochloride at a concentration of about 0.3-0.45 (w/w). In another embodiment, the Tris buffer system according to the invention includes tromethamine base at a concentration of about 0.465% (w/w) and tromethamine hydrochloride at a concentration of about 0.43% (w/w).

In some embodiments, the buffer system has a pH from about 7.5 to about 9.5, or a pH from about 8 to about 9, or a pH from about 8.2 to about 8.8. In one embodiment, the buffer system of the invention has a pH from about 8.4 to about 8.6.

In certain embodiments, the surfactant is a non-ionic surfactant. In some embodiments, the surfactant includes a multiplicity of ether linkages. Non limiting surfactants according to the invention, include without limitation, nonoxynol 12, PPG-12/PEG-50 Lanolin, or phospholipid CDM. When the surfactant is nonoxynol 12, it is present at a concentration of up to about 2.0% (w/w). In certain embodiments, nonoxynol 12 is present at a concentration of about 0.3-0.8%, most preferably of about 0.5% (w/w). When the surfactant is PPG-12/PEG-50 lanolin, it is present at a concentration of up to about 2.0% (w/w). In certain embodiments, PPG-12/PEG-50 lanolin is present at a concentration of about 0.3-0.8%, most preferably of about 0.5% (w/w). When the surfactant is phospholipid CDM, it is present at a concentration from about 0.2 to about 3% (w/w). In other embodiments, phospholipid CDM is present at a concentration of about 2% (w/w).

Wash solutions according to the instant invention include at least one metal ion chelating agent. Chelating agents are well known in the art. Non-limiting representative chelating agents suitable according to the invention include citric acid; phosphates; disodium EDTA; tetrasodium EDTA; ethylene glycol-bis-(b-aminoethylether)-N,N,N',N'-tetraacetic acid (EGTA); 1,2-bis(2-aminophenoxy)ethane-N,N,N',N'-tetraacetic acid (BAPTA); ethylene-N,N'-diglycine (EDDA); 2,2'-(ethylendiimino)-dibutyric acid (EBDA); lauroyl EDTA; dilauroyl EDTA, triethylene tetramine dihydrochloride (TRIEN), diethylenetriamin-pentaacetic acid (DPTA), triethylenetetramine hexaacetic acid (TTG), deferoxamine, Dimercaprol, zinc citrate, penicilamine succimer, Editronate, and edetate calcium disodium.

In particular embodiments, the metal ion chelating agent is tetrasodium EDTA at a concentration of from about 0.05% (w/w) to about 0.5% (w/w). In some embodiments, tetrasodium EDTA is present at a concentration of from about 0.1% (w/w) to about 0.15% (w/w). In another embodiment, tetrasodium EDTA is present at a concentration of about 0.126% (w/w).

Some wash solutions according to the invention may optionally include a preservative. Many preservative agents are well know to one of skill in the art. Preservatives which may be included according to the invention, include without limitation, imidazolindyl urea, benzalkonium chloride, diazolindinyl urea, dimethylol dimethylhydantoin, mixtures of 5-chloro-2-methyl-4-isothiazolin-3-one and 2-methyl-4-isothiazolin-3-one (also known as KATHON CG®), benzyl alcohol, phenylethyl alcohol, phospholid CDM, and chlorobutanol, parabens, benzoic acid, and sorbic acid.

In certain embodiments, the preservative is benzyl alcohol at a concentration of up to about 2% (w/w). In some embodiments, benzyl alcohol is present at a concentration of about 0.5-1.5% (w/w). In an embodiment, benzyl alcohol is present at a concentration of about 1.2% (w/w). In certain embodiments, the preservative is benzyl alcohol at a concentration of up to about 2% (w/w). In some embodiments, KATHON CG® is present at a concentration of up to 0.1% (w/w). In other embodiments, KATHON CG® is present at a concentration of about 0.05% (w/w).

In some embodiments, the tonicity of the solution is about 150-350 mOsmol, or about 200-300 mOsmol.

In a second aspect, the invention provides methods of using the solutions of the invention according to the first aspect for washing wounds, treating a topical microbial infection, and topically delivering a pharmaceutical agent to a tissue. The topical microbial infection may include, for example, a *Pseudomonas* infection of the ear or ear canal causing otitis externa.

DETAILED DESCRIPTION OF THE INVENTION

The present invention provides wash and carrier solutions ideally suited for topical administration as wash solutions for cleaning biological tissues and as carrier solutions for delivering pharmaceuticals to biological tissues. The solutions described herein are non-toxic, non-irritating, isotonic, possess non-specific broad-spectrum antimicrobial properties, and have an alkaline pH.

The solutions may be used, for example, to clean external surfaces to remove infectious agents or parasites at wound sites or to prepare tissue surfaces prior to surgeries. Thus, for example, the solutions may be used to wash biological tissues, such as bodily surfaces or orifices where there are infections or infestations of parasites (e.g., mammalian ears or ear canals infected or infested with mites or bacteria), or wounds where infectious agents may be present (e.g., bacterial or viral agents, which can enter the body through an open wound). Similarly, the solutions may be used to deliver pharmaceutically active agents to tissues by serving as biocompatible carriers which are chemically inactive with respect to the pharmaceutically active agent (e.g., antibiotics, antifungals). Because the solutions contain surfactants, they can be used as a solvent for pharmaceuticals that have limited solubility in aqueous solution and, therefore, are commercially distributed in solid or powder form.

The patent, scientific and medical publications referred to herein establish knowledge that was available to those of ordinary skill in the art at the time the invention was made. The patents and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

All technical and scientific terms used herein, unless otherwise defined below, are intended to have the same meaning as commonly understood by one of ordinary skill in the art; references to techniques employed herein are intended to refer to the techniques as commonly understood in the art, including variations on those techniques or substitutions of equivalent techniques which would be apparent to one of skill in the art.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of formulation chemistry include *Pharmaceutical Dosage Forms*, $2^{nd}$ Ed., Marcel Dekker, Inc., New York, (1990). Standard reference works setting forth the general principles of pharmacology include Goodman and Gilman's *The Pharmacological Basis of Therapeutics*, $10^{th}$ Ed., McGraw Hill Companies Inc., New York (2001). Any suitable materials and/or methods known to those of skill can be utilized in carrying out the present invention. However, preferred materials and methods are described. Materials, reagents, and the like to which reference are made in the following description and examples are obtainable from commercial sources, unless otherwise noted.

As used in this specification, the singular forms "a," "an" and "the" specifically also encompass the plural forms of the terms to which they refer, unless the content clearly dictates otherwise. For example, reference to "surfactant" includes mixtures of surfactants.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

In order to more clearly and concisely describe the subject matter which is the invention, the following definitions are provided for certain terms which are used in the specification and appended claims.

As used herein, the term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

In a first aspect the invention provides aqueous antimicrobial and preservative solutions which include a buffer system for maintaining the solution at an alkaline pH, a surfactant system, a metal ion chelating agent, and a non-ionic preservative having antimicrobial activity. Solutions according to this first aspect are non-irritating.

Buffer Systems

The use of an alkaline pH solution offers the advantage of increasing the transmembrane distribution and penetration of some drugs across the cell membrane. Most drugs are either weak acids or bases that form ionized and nonionized species in solution. The nonionized species are usually lipid soluble and are able to penetrate the lipid membrane of a cell whereas the ionized species have difficulty in crossing the cell membrane. At steady state, the acidic species will accumulate on the more basic side of the membrane while basic species tend to accumulate on the acidic side of the membrane. The alkaline nature of the wash solution of the instant invention should produce an external environment wherein the basic, ionized species of drugs should accumulate to the interior of the cell membrane. This occurs as a purely physical process that does not require active transport. Goodman and Gilman's *The Pharmacological Basis of Therapeutics*, $10^{th}$ Ed., Ch. 1., McGraw Hill Companies Inc., New York (2001). The exudates associated with infected lesions are acidic in nature and can inactivate or reduce the efficacy of many commonly used antibiotic agents. An alkaline pH wash solution can aid in the neutralization of the acidic environment of the lesion thereby allowing for increased efficacy for the commonly used antibiotic agents.

A characteristic of the solutions described lies in the buffer system selected to maintain the solution at an alkaline pH. As used herein, "alkaline pH" means a pH greater than 7.0. In some embodiments, the buffer solution is chosen to maintain the pH of the solution in the range of about 7.5 to about 9.5, or of about 8 to about 9, or of about 8.2 to about 8.8. In another embodiment, the buffer system of the invention maintains a pH from about 8.4 to about 8.6.

Buffer systems suitable for use in the present invention include any of those which are known in the art, or may hereafter be developed, and which can maintain the pH of the solution in the prescribed range for a substantial period of storage (e.g., two months storage at 40° C.). Suitable buffer systems include Tris buffer systems, phosphate buffer systems, citrate buffer systems, and any other basic amino acid buffer systems.

As used herein, the term "Tris buffer system" means an admixture in a solution of Tris base and hydrochloride in molar ratios which act to stabilize the pH of the solution. Tris is also known as tromethamine or trimethylol aminomethane or 2-amino-2-(hydroxymethyl)-1,3-propane-diol.

In some embodiments, the buffer system is a Tris buffer system, a phosphate buffer system, or a citrate buffer system. In certain embodiments, the buffer system is a Tris buffer system including tromethamine base at a concentration of about 0.1-2.0 (w/w) and tromethamine hydrochloride at a concentration of about 0.1-2.0 (w/w). In another embodiment the Tris buffer system according to the invention includes tromethamine base at a concentration of about 0.45-0.55 (w/w). In other embodiments, the Tris buffer system according to the invention includes tromethamine hydrochloride at a concentration of about 0.3-0.45 (w/w). In yet another embodiment, the Tris buffer system according to the invention includes tromethamine base at a concentration of about 0.465% (w/w) and tromethamine hydrochloride at a concentration of about 0.43% (w/w). Tris buffers are commercially available as, e.g., from Sigma Chemical Co., St. Louis, Mo.

As used herein, the term "phosphate buffer system" means an admixture in a solution of monosodium phosphate, disodium phosphate and/or trisodium phosphate in molar ratios which act to stabilize the pH of the solution.

As used herein, the term "citrate buffer system" means an admixture in a solution of citric acid and sodium hydroxide or citric acid and trisodium citrate or other equivalents in molar ratios which act to stabilize the pH of the solution.

Surfactants

In another aspect, the solutions of the present invention include a surfactant. As used herein, "surfactant" means a soluble compound that reduces the surface tension of liquids, or reduces interfacial tension between two liquids or a liquid and a solid. Surfactants are typically amphipathic compounds, such as detergents, having a polar and a non-polar group.

The surfactant is useful for removing or solubilizing oily, fatty, or waxy materials from the surface of a tissue. For example, by removing a layer of oil from skin, a pharmaceutical preparation applied topically to the skin can have more direct contact to the tissue and thereby be more effective. The surfactant can also increase the usefulness of the solution as a carrier by increasing the solubility of hydrophobic pharmaceuticals within the aqueous solution.

In some embodiments, the surfactant is a non-ionic surfactant. Non-ionic surfactants may be preferred because they cause less irritation to biological tissues. In some embodiments, the surfactant includes a multiplicity of ether linkages. Surfactants with ether linkages between the polar group and the non-polar group may be preferred because they are relatively more stable than ester linkages.

In some embodiments, the surfactant is at least one of nonoxynol 12 (Jeen International, Little Falls, N.J.), PPG-12/PEG-50 lanolin (Jeen International, Little Falls, N.J.), or phospholipid CDM, phospholipid EFA, phospholipid PTA (Uniquema, Paterson, N.J.) PEG-100 stearate, other nonoxynol or octoxynol surfactants with different PEG chain lengths. In other embodiments, the solution may contain two or more surfactants.

When the surfactant is nonoxynol 12, it is present at a concentration of up to about 2.0% (w/w). In some embodiments, nonoxynol 12 is present at a concentration of about 0.3-0.8%, most preferably of about 0.5% (w/w). When the surfactant is PPG-12/PEG-50 lanolin, it is present at a concentration of up to about 2.0% (w/w). In certain embodiments, PPG-12/PEG-50 lanolin is present at a concentration of about 0.3-0.8%, most preferably of about 0.5% (w/w). When the surfactant is phospholipid CDM, it is present at a concentration from about 0.2 to about 3% (w/w). In certain embodiments, phospholipid CDM is present at a concentration of about 2% (w/w). Phospholipid CDM is coco PG-dimonium chloride phosphate, a synthetic phospholipid surfactant.

One of skill in the art will appreciate that more than one surfactant may be included. Hence, in representative examples provided hereinafter, both nonoxynol 12 and PPG-12/PEG-50 lanolin are included.

Metal Ion Chelating Agents

In another aspect, the solutions of the present invention include a metal ion chelating agent. As used herein, the term "metal ion chelating agent" or simply, "chelating agent" means a chemical capable to sequester metal ions (such as for example magnesium and calcium ions) from a chemical or biological reaction mixture or solution by binding tightly to the metal ions thereby preventing them from participating in other chemical or biological reactions. The chelating agent is useful to remove magnesium and calcium ions from a solution or from the surface of a wound or tissue. Metal chelating agent can be useful in limiting the survival, growth or reproduction of microbes.

For example, a chelating agent can be used to chelate membrane-bound calcium and magnesium in Gram-negative bacilli (e.g., *Pseudomonas* species), weakening the bacterial membranes and thereby increasing the permeability of the bacterial membranes to antibiotics. Alternatively, or in addition, chelating agents such as EDTA (ethylene diamine tetra acetate (commercially available from various vendors including as VERSENE 100™ from Dow Chemical Co., Midland, Mich.)), can bind to and inactivate elastase on the surface of bacteria such as *Pseudomonas* species. Because the action of elastase is believed to be involved in the virulence of some bacteria by allowing them to dissolve the tight junctions between a host's epithelial cells, the chelating agent could reduce the virulence of such bacteria and be used in the treatment of such infections (e.g., otitis externa due to *Pseudomonas* infection).

Chelating agents are well known in the art. Acceptable chelating agents useful in the present invention include amino carboxylic acid compounds and pharmaceutically acceptable salts thereof. Non-limiting representative chelating agents suitable according to the invention include citric acid; phosphates; disodium EDTA; tetrasodium EDTA; ethylene glycol-bis-(b-aminoethylether)-N,N,N',N'-tetraacetic acid (EGTA); 1,2-bis(2-aminophenoxy)ethane-N,N,N',N'-tetraacetic acid (BAPTA); ethylene-N,N'-diglycine (EDDA); 2,2'-(ethylendiimino)-dibutyric acid (EBDA); lauroyl EDTA; dilauroyl EDTA, triethylene tetramine dihydrochloride (TRIEN), diethylenetriamin-pentaacetic acid (DPTA), triethylenetetramine hexaacetic acid (TTG), deferoxamine, Dimercaprol, zinc citrate, penicilamine succimer, Editronate, and edetate calcium disodium.

In particular embodiments, the metal ion chelating agent is tetrasodium EDTA at a concentration of from about 0.05% (w/w) to about 1.0% (w/w). In other embodiments tetrasodium EDTA is present at a concentration of from about 0.1% (w/w) to about 0.15% (w/w). In another embodiment, tetrasodium EDTA is present at a concentration of about 0.126% (w/w).

Preservatives

Some wash solutions according to the invention include a preservative with antimicrobial activity. As used herein, the term "preservative" means a compound that inhibits microbial growth, has antimicrobial activity, or otherwise inhibits the deterioration of a solution to which it is added. In some embodiments the preservative prevents the growth of microbes in the solution (to minimize or prevent back contamination from use to use and/or from user to user of a multidose dispenser filled with the solutions) and provide antimicrobial activity against microbes present at a wound or tissue.

Many preservative agents are well known to one of skill in the art. Preservatives which may be included according to the invention, include without limitation, imidazolindyl urea, benzalkonium chloride, diazolindinyl urea, dimethylol, mixtures of 5-chloro-2-methyl-4-isothiazolin-3-one (1.5% w/w) and 2-methyl-4-isothiazolin-3-one (0.35% w/w) (commercially available as KATHON CG® from Rohm Haas, Bayport, Tex.) dimethylhydantoin, benzyl alcohol (Velsicol Chemical, Rosemont, Ill.) phenylethyl alcohol, or chlorobutanol, parabens, benzoic acid, and sorbic acid. Also known in the art, surfactants may display antimicrobial preservative properties, e.g. phospholipid CDM.

As is known in the art, quaternary amines are also generally useful as preservatives. Non-limiting examples of quaternary amines include Quaternium-15 (Dow Chemical, Midland, Tex.), cetrimide and cetylpridinium chloride (Zeeland Chemicals, Zeeland, Mich.), imidazolidinyl urea (available as Germall 115, Sutton Labs, Chatham, N.J.), benzalkonium chloride (Stepan Co., Northfield, Ill.), and benzethonium chloride (Aldrich, Milwaukee, Wis.).

In certain embodiments, the preservative is benzyl alcohol at a concentration of up to about 2% (w/w). In some embodiments, benzyl alcohol is present at a concentration of about 0.5-1.5% (w/w). In an embodiment, benzyl alcohol is present at a concentration of about 1.2% (w/w). In certain embodiments, the preservative is benzyl alcohol at a concentration of up to about 2% (w/w). In some embodiment, KATHON CG® is present at a concentration of up to 0.1% (w/w). In another embodiment, KATHON CG® is present at a concentration of about 0.05% (w/w).

Preservatives according to the invention are either non-irritating by their nature or are present at a non-irritating concentration to normal or damaged tissues. Hence, for example benzyl alcohol, by its very nature is a potential irritant. However, it was unexpectedly found that (contrary to the teachings in the literature see *Handbook of Pharmaceutical Excipients*, 2$^{nd}$ Ed., Wade, A., and Weller, P., The Pharmaceutical Press, London GB, 1994, page 35-37) benzyl alcohol present at a non-irritating concentration is an antimicrobial preservative at an alkaline pH.

As used herein, "irritation" or "irritating" refers to a higher than normal sensitivity to external stimuli. In some instances, the tissue being treated may be inflamed and thus may present a heightened sensitivity or excitability such that the application of an ordinary stimulus produces pain or excessive action or reaction. "Non-irritating" means that the application of stimulus results in minimal pain or reaction.

In order to further minimize the potential for irritation, the solutions of the invention approach isotonicity. Solutions, which differ from normal serum in tonicity, have been shown to cause pain on injection, electrolyte shifts, or even tissue irritation following contact. This effect depends on the degree of deviation from isotonicity. For example, ophthalmic preparations for instillation in the eye should be isotonic in nature to avoid irritation. Therefore, wash solutions should be isotonic in nature to avoid exacerbation of irritation associated with tissue damage (see e.g., *Remington: The Science and Practice of Pharmacy*, 19$^{th}$ Ed., Chapt. 36, Gennaro, A. R., Ed, Mack Publishing Co. (1995)).

The tonicity of the solutions of the invention are about 150-350 mOsmol, or about 200 mM-300 mOsmol to reduce the likelihood or degree of irritation. As used herein, "isotonicity" means having the same concentration of solutes as found in blood. As such, an isotonic solution produces neither a net gain nor loss of water into cells exposed to such solution.

The solutions described herein may be dispensed from any dispenser as necessary to meet the specific contingencies. Those of skill will appreciate that the choice of dispenser size, shape and material may be dictated by a variety of parameters including the chemical nature of the components. For example, where benzyl alcohol is the preservative, high density polyethylene (HDPE) materials should be used.

In order to reduce the likelihood of infection of biological tissues, the solution may be prepared in a sterile environment and be maintained as a sterile solution until use. Hence, the invention provides a sterile preparation of antimicrobial wash and carrier solution as described above in a sterile airtight container. Such sterile preparations may be used in any of the methods described below.

In a second aspect, the invention provides methods of using the solutions of the invention according to the first aspect for washing wounds, treating a topical microbial infection, and topically delivering a pharmaceutical agent to a tissue.

The solutions, preparations, and methods may be used with any animal tissue, preferably any mammalian tissues including, but not limited to, human, non-human primate, equine, bovine, ovine, porcine, canine and feline tissues. The solutions may, for example, be used for the treatment of infections and infestations of the ear and ear canal in mammals, such as humans and dogs.

In another aspect, the invention provides a method of washing a wound using an antimicrobial wash and carrier solution as described above. The wound may be one that is known to be infected with microbes or susceptible to infection with microbes. The scope of the present invention contemplates the use of the solutions as a mouth rinse to inhibit the growth of infective lesions in the oral cavity, or as an immersion bath for treating superficial infective lesions of the skin (whole body) or an individual limb.

In another aspect, the invention provides a method of treating a topical microbial infection of a tissue by washing the tissue with an antimicrobial wash and carrier solution as described above. The topical microbial infection may include, for example, a *Pseudomonas* infection of the ear or ear canal causing otitis externa.

In another aspect, the invention provides a method of topically delivering a pharmaceutically active agent or medicament to a tissue by mixing the pharmaceutical agent with an antimicrobial wash and carrier solution as described above, and applying the resulting mixture to the tissue.

As used herein, "pharmaceutically active agent" or "medicament" shall refer to ophthalmic, dermatological, otic or nasal agents that can be topically applied. Preferred pharmaceutically active agents include antimicrobial agents (including antiviral agents, antifungal agents and bacteriocidal and bacteriostatic agents). Antibiotics are especially contemplated as pharmaceutically active agents in light of reported evidence of synergistic effects when using combinations of Tris-EDTA solutions with specific antibiotics (see for example Blue et al. (1974), Wooley et al. (1983), Farca et al. (1997), see also PCT/US01/29133).

Further non-limiting examples of pharmaceutically active agents according to this aspect of the invention include: muscarinics (e.g., pilocarpine), beta-blockers (e.g., betaxolol and timolol), anti-glaucoma agents, dopaminergic agonists and antagonists, prostaglandins, carbonic anhydrase inhibitors (e.g., acetazolamide, methazolamide and ethoxzolamide), non-steroidal and steroidal anti-inflammatories, such as suprofen, ketorolac, dexannethasone, rimexolone and tetrahydrocortisol, alpha adrenergic receptor agonists (e.g. para-amino clonidine, brimonidine), proteins, growth factors, anti-infective such as ciprofloxacin, and anti-allergic agents, (e.g. cromolyn sodium, emedastine and olopatadine). The invention also contemplates combinations of two or more pharmaceutically active agents.

Additionally, the formulations of the invention may include other optional ingredients such as for example, antioxidants, pharmaceutically acceptable buffers or excipients, pH adjusting or viscosity modifying or tonicity agents, drug carriers, sustained-release agents, comfort-enhancing agents, solubilizing aids, and other stabilizing agents.

In any of the foregoing methods, the solution may be applied by any standard means known to medical or veterinary professionals including, but not limited to, application by moistened swab, moistened cotton, moistened gauze, polymer foam, medically acceptable sponge or other cloth, syringe, squeeze bottle, dropper or pipette. Additionally, the solutions of the invention may be applied using gels or membrane films. The invention also contemplates the use of application methods and materials that are acceptable for oral administration into the mouth of the individual. The solution can also be poured directly onto the tissue from an open vessel or container, or can be placed into a tank or reservoir from which it is dispensed through a hose or nozzle, with or without added pressure. Application of the solutions under pressure through a hose or nozzle can be particularly useful for the irrigation and cleansing of tissues and wound sites.

The following examples are intended to further illustrate certain embodiments of the invention and are not limiting in nature. Those skilled in the art will recognize, or be able to ascertain, using no more than routine experimentation, numerous equivalents to the specific substances and procedures described herein. Such equivalents are considered to be within the scope of this invention, and are covered by the following claims.

EXAMPLES

Example 1

Antimicrobial Wash and Carrier Solutions

An antimicrobial wash and carrier solution according to the invention was made by standard methodologies familiar to any person of skill in the chemical arts. Generally, the steps are: (a) add the chelating agent (e.g., tetrasodium EDTA) to a beaker of $H_2O$ while stirring to solubilize; (b) add the buffer system (e.g., tromoethamine base and the tromoethamine HCl) while stirring to dissolve; (c) add the preservative (e.g., benzyl alcohol) while stirring; and (d) add surfactant (e.g., nonoxynol 12) while stirring; and (e) adjust the pH to the desired range (e.g., 7.5 to 9.5); finally (f) add $H_2O$ to the desired final volume.

| Ingredient | Amount (mg/g) | Preferred % Range (w/w) |
|---|---|---|
| Tromethamine Base | 46.5 | 0.3–0.6% |
| Tromethamine Hydrochloride | 43.0 | 0.3–0.6% |
| Tetrasodium EDTA | 12.6 | 0.05–0.2% |
| Nonoxynol 12 | 50 | 0.3–0.8% |
| PPG-12/PEG-50 Lanolin | 50 | 0.3–0.8% |
| Benzyl alcohol | 120 | 0.5–2.0% |
| Water Purified, USP | 9677.9 | — |

In this example, the tromethane (Tris) base and hydrochloride serve as the buffer system, the tetrasodium EDTA is the metal ion chelating agent, the nonoxynol 12 and PPG-12/PEG-50 Lanolin are both surfactants, and the benzyl alcohol is the preservative with antimicrobial activity.

Example 2

Additional Antimicrobial Wash and Carrier Solutions

Additional antimicrobial wash and carrier solutions according to the invention were prepared by the same protocol as described above to include the following materials:

| FORMULATION ID # | 940-16C | 940-6a | 940-8b | 940-12D | 940-14F |
|---|---|---|---|---|---|
| Tromethamine Base | 4.7 | 4.6 | 5.4 | 4.6 | 4.6 |
| Tromethamine Hydrochloride | 4.3 | 4.0 | 3.3 | 4.3 | 4.3 |
| Tetrasodium Edetate | 1.3 | 1.2 | 1.2 | 1.3 | 1.3 |
| Nonoxynol 12 | 5 | 0 | 0 | 0 | 1 |
| PPG-12/PEG-50 Lanolin | 5 | 0 | 0 | 0 | 5 |
| Phospholipid CDM | 0 | 20 | 20 | 20 | 0 |
| Benzyl alcohol | 12 | 0 | 0 | 0 | 12 |
| Kathon CG ® | 0 | 0.5 | 0 | 0 | 0 |
| Water Purified, USP QS AD | 1000 | 1000 | 1000 | 1000 | 1000 |
| pH | 8.5 | 8.0 | 8.6 | 8.2 | 8.1 |

Example 3

Antimicrobial Effectiveness of Benzyl Alcohol

Various concentrations of benzyl alcohol were tested for antimicrobial preservative effectiveness (APE) using the USP 25 test 51 (U.S. Pharmacopeia 25, U.S. Pharmacopeia, MD (2001)). The formulations below are based on the formulation designated as 940-16 C (with a slightly higher pH) in Example 2 above with varying benzyl alcohol concentrations. The table below summarizes the results of these studies.

| Sample ID | Benzyl alcohol | pH | APE results |
|---|---|---|---|
| 940-19A | 1.20% w/w | 8.60 | Pass |
| 940-19B | 0.96% w/w | 8.60 | Pass |
| 940-19C | 0.70% w/w | 8.68 | Pass |

(*) see Example 2

These results are surprising in that the prior art teaches that benzyl alcohol does not have significant preservative activity at a pH above 8.0. Indeed, it is generally taught in the art that many preservatives are not effective at alkaline pH. For example, sorbic acid and salicylic acid are active as antimicrobial preservatives only in the acidic pH range of about 4.0-6.0. Similarly, benzoyl alcohol, 2-phenoxyethanol, and benzoic acid are typically used only in the acidic pH range of about 4.0-5.0 and are not effective at a pH above 8.0 (see, *Handbook of Pharmaceutical Excipients* (2nd edition, 1994), A. Wade and P. J. Weller, eds., pg. 35). However, as the above data demonstrate, benzyl alcohol at pH 8.5 meets the USP antimicrobial preservative requirement.

A comparison study shows that, when the various concentrations of benzyl alcohol are tested for antimicrobial preservative effectiveness (APE), the addition of benzyl alcohol produces both enhanced antimicrobial activity and prolonged shelf life as compared to solutions of the instant invention lacking benzyl alcohol.

Antimicrobial activity can be measured by any standard assay known to those of skill in the art (e.g., USP 25 antimicrobial preservative effectiveness (APE) test 51 (U.S. Pharmacopeia 25, U.S. Pharmacopeia, MD (2001)).

Example 4

Otitis Externa—Animal Studies

Representative solutions of the instant invention were tested as a pretreatment for the manifestations of otitis externa prior to other medication in 50 animals, mostly dogs, ranging from 6 months to 15 years of age. The solution was instilled into the ear canals followed by gentle massage. Instillation and massage occurred 10-15 minutes prior to any additional medication. The manifestations of otitis externa were attributed to food allergies, recurrent Malassezia otitis, staphylococcus/streptococcus/pseudomonas otitis, otitis with exudate, pruritus, erythematous otitis, atopy, ear mites, ruptured tympanic membrane, excoriation, ulceration, chronic recurrent otitis with hyperplasia, hematoma, and pemphigous foliaceus.

No irritation was reported in 49 of the 50 animals examined (one animal lost to study). In four of the 50 animals tested, the solution of the instant invention was the sole medication. Of these four animals, three had 100% resolution of the symptoms of otitis externa following 14 days of treatment. The remaining animal had a 50% resolution of symptoms when the owner removed the animal from the study.

Complete resolution of symptomology occurred when the instant invention was used in conjunction with the following commonly used agents: Zeniquin (marbofloxacin), Clovamox (amoxycillin trihydrate/clavulanate potassium), hydrocortison, prednisone, Tresaderm (thiabendazole-dexamethasone-neomycin sulfate solution), neomycin/polymixin drops, Otomax (gentamicin sulfate, betamethasone vakerate, clotrimazole), Baytril Otic (enroflozacin/silver sulfadiazine), Conofite (miconazole nitrate), and Gentocin otic (gentamicin sulfate/betamethasone valerate).

Example 5

Antimicrobial Properties

To illustrate the antimicrobial properties of representative solutions of the invention, the resolution of the bacterial infections associated with the otitis externa for the four animals treated only with the representative solution of the invention (see Example 4) are described herein.

| Subject | Type | History | Microbiology at Onset | Treatment | Resolution (%) |
|---|---|---|---|---|---|
| 7 | Mixed K-9 | Ear mites | Gram (+) cocci culture S. intermedius | 14 days | 100* |
| 9 | Dalmatian | Atopic dermatitis | Gram (+) cocci culture | 14 days | 100* |
| 10 | English Mastiff | Pruritic skin disease | Gram (+) cocci culture | 10 days | 100* |
| 13 | Cocker Spaniel | Invasive lymphoma | Gram (+) cocci culture & Malassezia | 21 days | 50** |

*= Negative bacterial cytology at cessation of treatment and 1 week post treatment
**= Cocci still present when animal removed from study by owner Example 6

Antimicrobial Properties

The antimicrobial activity of the commercial product T8 Solution™ prepared as per Example 1, (DVM Pharmaceuticals, Inc., Miami, Fla.) was compared versus the antimicrobial activity of a T8 Solution placebo and the commercial product TRIZ EDTA™ (533 mg TRIS, 141 mg EDTA, 112 ml $H_2O$, buffered to pH 8.0, DermaPet, Inc. Potomac, Md.). The antimicrobial activity was evaluated against eight organisms *Escherichia coli, Candida albicans, Pseudomonas aeruginosa, Staphylococcus aureus, Klebsiella oxytoca, Proteus mirabilis, Proteus vulgaris* and *Staphylococcus intermedius*.

Test organisms were obtained from the American Type Culture Collection (ATCC), Manassas, Va. and stored at low temperature (−70° C.) until used. The test included eight microbial strains: *Candida albicans* ATCC10231, *Pseudomonas aeruginosa* ATCC 9027, *Proteus mirabilis* ATCC 33583, *Proteus vulgaris* ATCC 6383, *Escherichia coli* ATCC 8739, *Staphylococcus aureus* ATCC 6538, *Staphylococcus intermedius* ATCC 29663 and *Klebsiella oxytoca* ATCC 49473. Each organism was evaluated separately as opposed to a mixed culture inoculum evaluation.

Stock cultures were maintained on Soybean-Casein Digest Agar (SCDA) slants for bacteria and Sabouraud Dextrose Agar (SDA) slants for fungi. Test cultures were prepared either on SCDA plate (bacteria) or SDA plate (fungi) as per USP 51 methodology, harvested, and adjusted to about $10^8$ microorganism per ml for each test culture.

The number of colony-forming units (cfu) per ml in each microbial suspension was determined immediately using standard plate-count techniques, appropriate media, incubation time and temperature ((USP Test Method 61, U.S. Pharmacopeia 25, U.S. Pharmacopeia, MD (2001)). This value served to determine the inoculum size used for the test.

A normal saline solution (0.9% sodium chloride) was used as suspending and diluting fluid for bacterial and yeast cultures. A Soybean-Casein Digest Broth supplemented with 4.0% Polysorbate-20 and 1% Lecithin was used as product diluent. SCDA was used as culture media for bacterial count and SDA was used as culture media for fungi count.

Three samples (products) were tested for the study, T8 Solution™ (Lot V2C020A, DVM Pharmaceuticals, Inc. Miami, Fla.), T8 Solution Placebo (Lot 940-19D, DVM Pharmaceuticals, Inc. Miami, Fla.), and Triz EDTA™ (Lot 21068, DermaPet, Inc. Potomac, Md.). Both T8 Solution™ and the T8 Solution placebo were used as is. The T8 Solution placebo does not contain benzyl alcohol. Triz EDTA™ was reconstituted as per the label instructions before use.

Test samples were inoculated with a suspension (no more than 0.1 ml) of one of the test organisms to give a final microbial concentration of about $10^5$ to about $10^6$ microorganisms per ml of the preparation. The samples were mixed thoroughly to ensure homogeneous distribution. The inoculated samples were incubated at 22.5±2.5° C., and protected from light for 42 days.

Samples were removed from each tube at 24, 72 hours and after 7, 14, 21, 28 and 42 day incubation and the number of viable microorganisms determined using the standard plate count technique.

The USP requirement antimicrobial effectiveness for bacteria is "No less than 2.0 log reduction from the initial count at 14 days, and no increase from the 14 days" count at 28 days and for fungi: "No increase from the initial calculated count at 14 and 28 days."

Both T8 Solution™ and T8 Solution placebo met the USP 26 Test 51 Antimicrobial Effectiveness Testing for all 8 microorganisms tested.

Under the same experimental conditions, Triz-EDTA™ failed the USP testing for *S. aureus* and *Klebsiella oxytoca*. Triz EDTA™ failed to meet the "two log reduction within 14 days" requirement. (less than 1% of initial counts). Triz EDTA™ did meet the USP 26 Test 51 Antimicrobial Effectiveness test standard for *E. coli, S, intermedius, P. aeruginosa, C. albicans, Proteus mirabilis* and *Proteus vulgaris*.

The rate of microbial count reduction for T8 Solution™ was significantly greater than the T8 Solution placebo or Triz-EDTA™. *E. coli, P. aeruginosa, Klebsiella oxytoca, Proteus mirabilis* and *Proteus vulgaris* were reduced by T8 Solution™ to a non-detectable level (<10 cfu/g, colony forming units per gram of sample) within 24 hours. Both *S. aureus* and *S. intermedius* were reduced by T8 Solution™ to a non-detectable level within 72 hours. *Candida albicans* was reduced by T8 Solution™ to less than one percent of initial counts within 24 hours and to non-detectable level within 14 days.

The number of viable microorganisms initially present at the start of the tests and the number of viable microorganisms detected at the specified intervals, for the eight test organisms are given in Tables I-VIII.

TABLE I

Number of viable microorganisms present at the indicated time intervals (cfu/ml).
Organism: *Escherichia coli*

|  | Inoculum | 24 hrs | 72 hrs | 7 days | 14 days | 21 days | 28 days | 42 days |
|---|---|---|---|---|---|---|---|---|
| T8 | 580,000 | <10 | <10 | <10 | <10 | <10 | <10 | <10 |
| T8 placebo | 580,000 | 4300 | 5 | <10 | <10 | <10 | <10 | <10 |
| Triz EDTA | 580,000 | 7250 | 350 | 100 | <10 | <10 | <10 | <10 |

TABLE II

Number of viable microorganisms present at the indicated time intervals (cfu/ml).
Organism: *Ps. aeruginosa*

|  | Inoculum | 24 hrs | 72 hrs | 7 days | 14 days | 21 days | 28 days | 42 days |
|---|---|---|---|---|---|---|---|---|
| T8 | 150,000 | <10 | <10 | <10 | <10 | <10 | <10 | <10 |
| T8 placebo | 150,000 | <10 | <10 | <10 | <10 | <10 | <10 | <10 |
| Triz EDTA | 150,000 | <10 | <10 | <10 | <10 | <10 | <10 | <10 |

Table III

Number of viable microorganisms present at the indicated time intervals (cfu/ml).
Organism: *S. aureus*

|  | Inoculum | 24 hrs | 72 hrs | 7 days | 14 days | 21 days | 28 days | 42 days |
|---|---|---|---|---|---|---|---|---|
| T8 | 345,000 | 100 | <10 | <10 | <10 | <10 | <10 | <10 |
| T8 placebo | 345,000 | 298,000 | 265,000 | 116,500 | 1350 | <100 | <10 | <10 |
| Triz EDTA | 345,000 | 238,000 | 222,500 | 192,500 | 185,000 | <100 | <10 | <10 |

TABLE IV

Number of viable microorganisms present at the indicated time intervals (cfu/ml).
Organism: *Klebsiella oxytoca*

|  | Inoculum | 24 hrs | 72 hrs | 7 days | 14 days | 21 days | 28 days | 42 days |
|---|---|---|---|---|---|---|---|---|
| T8 | 265,000 | <10 | <10 | <10 | <10 | <10 | <10 | <10 |
| T8 placebo | 265,000 | 20 | 10 | <10 | <10 | <10 | <10 | <10 |
| Triz EDTA | 265,000 | 73,500 | 67,500 | 56,000 | 19,500 | 2050 | 140 | <10 |

TABLE V

Number of viable microorganisms present at the indicated time intervals (cfu/ml)
Organism: *Proteus mirabilis*

|  | Inoculum | 24 hrs | 72 hrs | 7 days | 14 days | 21 days | 28 days | 42 days |
|---|---|---|---|---|---|---|---|---|
| T8 | 620,000 | <10 | <10 | <10 | <10 | <10 | <10 | <10 |
| T8 placebo | 620,000 | 26,500 | 600 | 400 | 5 | <10 | <10 | <10 |
| Triz EDTA | 620,000 | 43,000 | 15,000 | 8,500 | 7,500 | 800 | 600 | <10 |

TABLE VI

Number of viable microorganisms present at the indicated time intervals (cfu/ml).
Organism: *Proteus vulgaris*

|  | Inoculum | 24 hrs | 72 hrs | 7 days | 14 days | 21 days | 28 days | 42 days |
|---|---|---|---|---|---|---|---|---|
| T8 | 455,000 | <10 | <10 | <10 | <10 | <10 | <10 | <10 |
| T8 placebo | 455,000 | 3050 | <100 | <10 | <10 | <10 | <10 | <10 |
| Triz EDTA | 455,000 | 24,000 | 300 | 40 | <10 | <10 | <10 | <10 |

TABLE VII

Number of viable microorganisms present at the indicated time intervals (cfu/ml).
Organism: *Staph, intermedius*

|  | Inoculum | 24 hrs | 72 hrs | 7 days | 14 days | 21 days | 28 days | 42 days |
| --- | --- | --- | --- | --- | --- | --- | --- | --- |
| T8 | 240,000 | 2050 | <10 | <10 | <10 | <10 | <10 | <10 |
| T8 placebo | 240,000 | 316,000 | 118,500 | 102,500 | <100 | <10 | <10 | <10 |
| Triz EDTA | 240,000 | 348,000 | 334,000 | 297,500 | 1300 | <10 | <10 | <10 |

TABLE VIII

Number of viable microorganisms present at the indicated time intervals (cfu/ml).
Organism: *C. albicans*

|  | Inoculum | 24 hrs | 72 hrs | 7 days | 14 days | 21 days | 28 days | 42 days |
| --- | --- | --- | --- | --- | --- | --- | --- | --- |
| T8 | 610,000 | 3550 | 1200 | 25 | <10 | <10 | <10 | <10 |
| T8 placebo | 610,000 | 145,500 | 101,000 | 41,000 | 3400 | 800 | 190 | 20 |
| Triz EDTA | 610,000 | 138,500 | 130,000 | 41,500 | 1950 | 375 | 45 | <10 |

EQUIVALENTS

While this invention has been particularly shown and described with references to embodiments thereof, it will be understood by those skilled in the art that various changes in form and details may be made therein without departing from the spirit and scope of the invention as defined by the appended claims. Those skilled in the art will recognize, or be able to ascertain using no more than routine experimentation, many equivalents to the specific embodiments of the invention described specifically herein. Such equivalents are intended to be encompassed in the scope of the appended claims.

What is claimed is:

1. A method of washing a wound comprising washing the wound with an aqueous antimicrobial and preservative alkaline solution, said solution comprising:
    (a) a buffer system comprising a Tris buffer system for maintaining the solution at a pH in a range of about 8 to about 9.5;
    (b) a non-ionic surfactant system comprising at least one surfactant having a multiplicity of ether linkages;
    (c) metal ion chelating agent comprising EDTA or its pharmaceutically acceptable salts; and
    (d) a non-ionic preservative having anti-microbial activity comprising benzyl alcohol wherein the concentration of benzyl alcohol is about 0.5% (w/w) to about 2.0% (w/w),
wherein the solution has a pH in the range of about 8 to about 9.5 and has anti-microbial properties, and the aqueous anti-microbial and preservative alkaline solution is non-irritating.

2. The method of claim 1, wherein the buffer system is a Tris buffer system comprising tromethamine base at a concentration of about 0.3 to about 0.55% (w/w) and tromethamine hydrochloride at a concentration of about 0.3 to about 0.45% (w/w).

3. The method of claim 1, wherein the surfactant is selected from the group consisting of nonoxynol 12, PPG-12/PEG-50 lanolin, phospholipid CDM, phospholipid EFA, phospholipid PTA, PEG-100 stearate, and any other nonoxynol, octoxynol surfactants with different PEG chain lengths.

4. The method of claim 1, wherein the metal ion chelating agent is selected from the group consisting of disodium EDTA, tetrasodium EDTA, lauroyl EDTA, dilauroyl EDTA and edetate calcium disodium.

5. A method of treating a topical microbial infection of a tissue comprising washing the tissue with an aqueous antimicrobial and preservative alkaline solution, said solution comprising:
    (a) a buffer system comprising a Tris buffer system for maintaining the solution at a pH in a range of about 8 to about 9.5;
    (b) a non-ionic surfactant system comprising at least one surfactant having a multiplicity of ether linkages;
    (c) metal ion chelating agent comprising EDTA or its pharmaceutically acceptable salts; and
    (d) a non-ionic preservative having anti-microbial activity comprising benzyl alcohol wherein the concentration of benzyl alcohol is about 0.5% (w/w) to about 2.0% (w/w),
wherein the solution has a pH in the range of about 8 to about 9.5 and has anti-microbial properties, and the aqueous anti-microbial and preservative alkaline solution is non-irritating.

6. A method of preparing a tissue for surgery comprising washing the tissue prior to the surgery with an aqueous anti-microbial and preservative alkaline solution, said solution comprising:
    (a) a buffer system comprising a Tris buffer system for maintaining the solution at a pH in a range of about 8 to about 9.5;
    (b) a non-ionic surfactant system comprising at least one surfactant having a multiplicity of ether linkages;
    (c) metal ion chelating agent comprising EDTA or its pharmaceutically acceptable salts; and
    (d) a non-ionic preservative having anti-microbial activity comprising benzyl alcohol wherein the concentration of benzyl alcohol is about 0.5% (w/w) to about 2.0% (w/w),
wherein the solution has a pH in the range of about 8 to about 9.5 and has anti-microbial properties, and the aqueous anti-microbial and preservative alkaline solution is non-irritating.

7. A method of topically delivering a pharmaceutical agent to a tissue comprising:
    (a) mixing the pharmaceutical with an aqueous antimicrobial and preservative alkaline solution, said solution comprising:

(i) a buffer system comprising a Tris buffer system for maintaining the solution at a pH in a range of about 8 to about 9.5;
(ii) a non-ionic surfactant system comprising at least one surfactant having a multiplicity of ether linkages;
(iii) metal ion chelating agent comprising EDTA or its pharmaceutically acceptable salts; and
(iv) a non-ionic preservative having anti-microbial activity comprising benzyl alcohol wherein the concentration of benzyl alcohol is about 0.5% (w/w) to about 2.0% (w/w),
wherein the solution has a pH in the range of about 8 to about 9.5 and has anti-microbial properties, and the aqueous antimicrobial and preservative alkaline solution is non-irritating; and
(b) applying the resulting mixture to the tissue.

8. A method of washing a wound comprising washing the wound with an aqueous antimicrobial and preservative alkaline solution, said solution comprising:

(a) a buffer system comprising a Tris buffer system for maintaining the solution at a pH in a range of about 8.2 to about 8.8;
(b) a surfactant system comprising at least one surfactant having a multiplicity of ether linkages;
(c) metal ion chelating agent comprising EDTA or its pharmaceutically acceptable salts at a concentration of about 0.05 wt. % to about 0.15 wt. %; and
(d) a non-ionic preservative having anti-microbial activity comprising benzyl alcohol at a concentration of about 0.5% (w/w) to about 2% (w/w),
wherein the solution has a pH in the range of about 8.2 to about 8.8 and has anti-microbial properties, and the aqueous antimicrobial and preservative alkaline solution is non-irritating.

* * * * *